(12) United States Patent
Lakshminarayan et al.

(10) Patent No.: US 8,706,203 B2
(45) Date of Patent: Apr. 22, 2014

(54) CLASSIFICATION OF A SIGNAL IN A TIME DOMAIN

(75) Inventors: Choudur Lakshminarayan, Austin, TX (US); Alexander Singh Alvarado, Mountain View, CA (US); Jose Carlos Principe, Gainesville, FL (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 68 days.

(21) Appl. No.: 13/459,952

(22) Filed: Apr. 30, 2012

(65) Prior Publication Data

US 2013/0289426 A1 Oct. 31, 2013

(51) Int. Cl.
*A61B 5/0428* (2006.01)
(52) U.S. Cl.
USPC .......................................................... 600/509
(58) Field of Classification Search
USPC .......................................... 600/508, 523, 509
See application file for complete search history.

(56) References Cited

U.S. PATENT DOCUMENTS 7,630,756 B2 12/2009 Linker
7,667,624 B2 2/2010 Stoval

2010/0303101 A1* 12/2010 Lazar et al. ................... 370/521
2011/0184297 A1 7/2011 Vitali et al.
2011/0208079 A1 8/2011 Babaeizadeh et al.

OTHER PUBLICATIONS

Aurel A. Lazar, "Time encoding with an integrate-and-fire neuron with a refractory period", Science Direct, Jun. 2004 (6 pages).
C. Costa Santos, et al., "Clustering Fetal Heart Rate Tracings by Compression", IEEE Computer Society, Retrieved from: http://arxiv.org/ftp/q-bio/papers/0612/0612013.pdf, Accessed Apr. 30, 2012 (6 pages).
Aurel A. Lazar, et al., "Encoding Natural Scenes with Neural Circuits with Random Thresholds", Vision Research, Nov. 30, 2012 (32 pages).
Jenna Wiens, et al, "Active Learning Applied to Patient-Adaptive Heartbeat Classification", Retrieved from: http:// web.mit.edu/jwiens/www/NIPS2010.pdf, Accessed: Apr. 30, 2012 (9 pages).

\* cited by examiner

*Primary Examiner* — George Evanisko

(57) ABSTRACT

Methods, systems, and computer-readable and executable instructions are provided for classifying an electrocardiogram (ECG) signal. Classifying an ECG signal can include analyzing the ECG signal using a stream of pulses generated by a sampler, extracting cardiac pulse features from a timing of the stream of pulses, and classifying the ECG signal based on the extracted cardiac pulse feature.

12 Claims, 3 Drawing Sheets

CLASSIFICATION OF A SIGNAL IN A TIME DOMAIN

BACKGROUND

Heart function measured by electrocardiograms (ECG) is crucial for patient care. ECG generated waveforms are used to find patterns of irregularities in cardiac cycles in patients. Irregularities can evolve over an extended period of time, which can require continuous monitoring.

DETAILED DESCRIPTION

Figure 1:
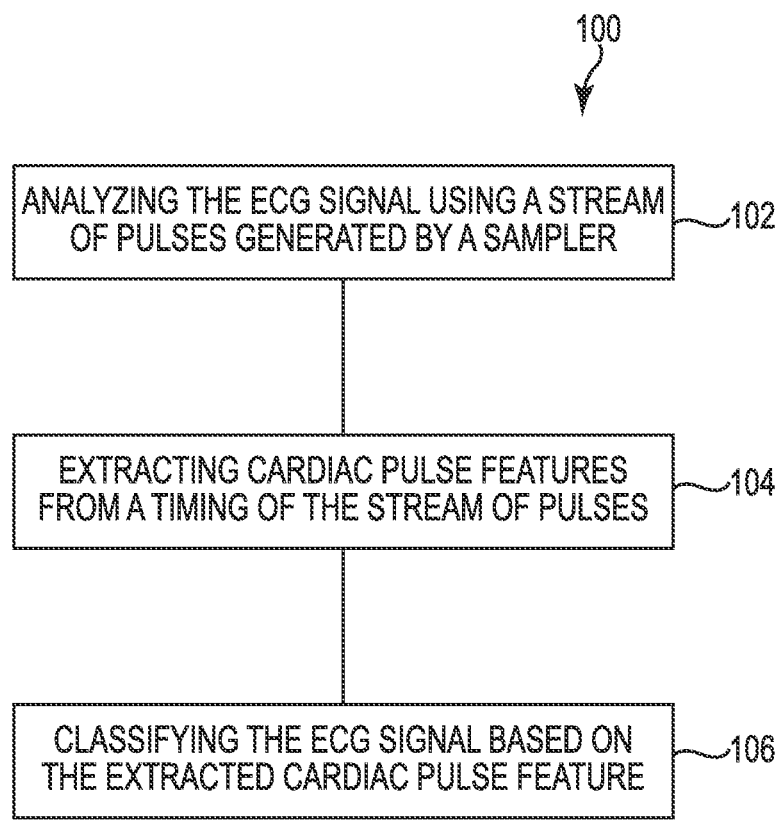
FIG. 1 is a block diagram illustrating an example of a method for classifying an electrocardiogram (ECG) signal according to the present disclosure.

Examples of the present disclosure may include methods, systems, and computer-readable and executable instructions and/or logic. An example method for classifying an electrocardiogram (ECG) signal can include analyzing the ECG signal using a stream of pulses generated by a sampler, extracting cardiac pulse features from a timing of the stream of pulses, and classifying the ECG signal based on the extracted cardiac pulse feature.

An ECG is a graphic representation of a heart's electrical activity, formed as cardiac cells depolarize and repolarize. An ECG cycle can be separated into various electrical waves (e.g., P, Q, R, S, and T). A P wave marks activation of the atria, and a QRS complex can represent an activation of the left ventricle and the right ventricle. A heart beat cycle can be measured as the time between the second of the three parts of the QRS complex, in other words the distance between consecutive R peaks. During the QRS complex, the atria prepare for the next beat, and the ventricles relax in the T wave.

Patterns of irregularities and other cardiac issues may necessitate continuous monitoring, and this continuous monitoring of cardiac functions may require a wireless ECG recording device. However, the wireless device may consist of an enclosed system including electrodes, processing circuitry, and a wireless communication block imposing constraints on area, power, bandwidth, and resolution.

Additionally, challenges to ECG signal classification can create difficulty during continuous cardiac function monitoring. Classification of ECG signals can include extracting cardiac features (e.g., cardiac pulse features) from ECG signals, and challenges can include within-patient and between-patient variability in timing profiles and morphology of damaged cardiovascular processes. Classification techniques that use traditional methods of classification may fail when applied to a new patient, for example.

As discussed further herein with respect to the present disclosure, time-based compression and classification of heartbeats can provide continuous monitoring of cardiac functions for real time diagnostics by combining compression and analysis of heartbeats, and diagnostics can be performed directly in a pulse domain allowing for classification while avoiding a need for signal reconstruction. A sampler, as will be discussed further herein, is used to transform a continuous patient information input into a set of events. These events, also known as pulses and/or samples, can carry the input into a "timing". The pulse domain can include anything that operates on the pulses directly, without the need of transforming and/or reconstructing the pulse (e.g., determining an original continuous signal from a sequence of samples). The timing can include an exact timing of each event, and the distribution of these timings can include heartbeat information.

In some embodiments, time-based compression and classification of heartbeats can also result in reduced constraints (e.g., power, bandwidth, and/or area constraints) when working with a wireless ECG device, for example.

In the following detailed description of the present disclosure, reference is made to the accompanying drawings that form a part hereof, and in which is shown by way of illustration how examples of the disclosure may be practiced. These examples are described in sufficient detail to enable those of ordinary skill in the art to practice the examples of this disclosure, and it is to be understood that other examples may be utilized and the process, electrical, and/or structural changes may be made without departing from the scope of the present disclosure.

The figures herein follow a numbering convention in which the first digit or digits correspond to the drawing figure number and the remaining digits identify an element or component in the drawing. Similar elements or components between different figures may be identified by the use of similar digits. Elements shown in the various examples herein can be added, exchanged, and/or eliminated so as to provide a number of additional examples of the present disclosure.

In addition, the proportion and the relative scale of the elements provided in the figures are intended to illustrate the examples of the present disclosure, and should not be taken in a limiting sense. As used herein, the designators "N", "P," "R", and "S" particularly with respect to reference numerals in the drawings, indicate that a number of the particular feature so designated can be included with a number of examples of the present disclosure. Also, as used herein, "a number of" an element and/or feature can refer to one or more of such elements and/or features.

In some embodiments of the present disclosure, time-based encodings (e.g., level crossing samplers, asynchronous sigma delta encoders, and/or reference crossing samplers) of ECG recordings can be used to perform classification of normal heartbeats and irregular heartbeats known as arrhythmias. The time-based encodings (e.g., representations) can be used to extract discriminative features from the ECG recordings, without a need for signal reconstruction. Signal reconstruction can include determining an original continuous signal from a sequence of samples, can be time-consuming, and may require increased bandwidth.

While the examples are discussed in the present disclosure in reference to ECG signals, embodiments are not limited to these examples. Embodiments described herein for classification of a signal in a time domain can additionally apply to seismic signals used in oil and gas exploration, Electroencephalography (EEG) signals, data center monitoring signals, e.g., processor and memory resource utilization signals, etc.

FIG. 1 is a block diagram illustrating an example of a method 100 for classifying an ECG signal according to the present disclosure. An ECG signal can be gathered from an ECG recording collected from a patient, and/or a number of ECG signals can be collected from a number of ECG recordings collected from a number of patients. In a number of embodiments, the ECG recording can include a time-delayed recording (e.g., a past recording) and/or a real-time recording (e.g., sensing at substantially a same time the cardiac pulse events defining the signal occur). The recordings can be preprocessed to attenuate an effect of a number of artifacts including, for example, power line interference, contact noise, motion, electromyographic noise, and/or baseline drift, among others.

To preprocess the recordings, recorded data can be passed through a median filter (e.g., a filter with a 200 ms window size) to remove P-waves and QRS complexes, for example. A second median filter (e.g., a filter with a 600 ms window size) to remove T-waves. The filtered signal can represent a baseline, which can be subtracted from the original, non-filtered recording. A notch filter (e.g., centered at 60 Hz) can be implemented through a finite impulse response filter (e.g., a 60 tap finite impulse response filter) in order to remove power line interference.

Characteristic features in ECG recordings can be localized in time and high amplitudes. Therefore, a preprocessed signal can be compressed using an adaptive sampler. An adaptive sampler can allow for a number of samples per second to change, as compared to a fixed sampler, where a number of samples per second will not change. An ECG recording may include, for example, a number of signals that are less important than others when classifying an ECG signal. For example, a particular occurrence between heartbeats may not be as important to the classification as a heartbeat itself, and therefore, sampling can be concentrated in the shape and not the in-between regions. As a result, a number of samples per second can be reduced without a loss of discriminability.

The compressed data representation can include discriminative information about input data (e.g., discriminability in heartbeat shapes in patients) that can be accessed (e.g., accessed directly) in a pulse domain without having to reconstruct the signal, and/or based on a pulse representation. Samples generated by an Integrate and Fire (IF) scheme, (e.g., and IF sampling scheme) can be used directly in order to discriminate different inputs. For example, cardiac features (e.g., P wave, QRS complex, R peak, T wave, etc.) can be obtained directly from a compressed representation, avoiding reconstruction.

The compressed data can be transformed into a time-based data representation, and the data representation can be encoded using a sampling scheme, as will be discussed further herein. The time-based data representation can include an output of the sampler (e.g., the pulses, also known as samples and/or events). In a number of embodiments, the IF sampling scheme can be utilized, but embodiments are not limited to such a sampling scheme.

Samples and/or events (e.g., within the time-based representation) can occur at any time and may not be bound to a uniform grid, as compared to conventional analog to digital converters. Therefore, rather than representing continuous input in a numeric value of uniform samples, information can be represented not in the values of the sample, but in a location of the discrete events.

At 102, the ECG signal is analyzed using a stream of pulses generated by the sampler (e.g., the IF sampler). The stream of pulse can be the output (e.g., events) of an IF sampler, and the stream of pulses can adapt to changes in heartbeat shapes and/or heartbeat rhythms, for example. At 104, cardiac pulse features are extracted from a timing of the stream of pulses. In some embodiments, cardiac pulse features can include bin counts, as will be discussed further herein. In a number of examples, cardiac features can further include pulse counts, pulse density, and/or learned models describing heartbeat data. In some embodiments, the cardiac features can be dependent on a user and/or patient, for example.

For example, a heartbeat can be monitored, and can include a time, for example, from zero to some time, t. Intervals can be created within the heartbeat, and within those intervals, bins can be created. Events within each bin can be counted, and the bins and/or events within the bin can be referred to as a feature. This can allow for the creation of a representation allowing for a comparison of two or more sampled heartbeats. Each heartbeat may have a different number of events, and by binning, each heartbeat can be represented by N bins.

At 106, the ECG signal is classified based on the extracted cardiac pulse feature. Classification can include the analysis of cardiac features, also known as regions in a cardiac beat, including a P wave, a QRS complex, an R peak, and a T wave, among others. In some examples of the present disclosure, a bin, which will be discussed further herein, can be a cardiac pulse feature. In a number of embodiments, a linear discriminant classifier (LDA) is used in classification. The use of an LDA can include, for example, finding a linear combination of features which characterizes or separates of objects or events (e.g., cardiac events).

In classification of patient heartbeats, due to an inherent variability across and/or within patients, a patient's unique heartbeat data can be combined with a global set (e.g., global training set) of features of all patients to perform classification. The global training set can include a database of patient information, for example. Training samples from the test patient, also known as a local training set, may be given higher importance than those in a global training set. To do so, parameters for LDA classifiers can be learned, based on the local $$\left(\mu_k^l, \sum_k^l\right)$$

and global $$\left(\mu_k^g, \sum_k^g\right)$$

parameters estimated from the training sets. The estimated parameters can be combined linearly, such that:

$$\mu_k = K_k \mu_k^g + (1-K_k)\mu_k^l \text{ and } \sum_k = K_k \sum_k^g + (1-K_k)\sum_k^l.$$

where k can represent a class (e.g., N, S, V, Q heartbeats), g can represent a parameter and/or parameters from the global training set, and l can represent a parameter and/or parameters from the local training set, for example.

In some embodiments of the present disclosure, available ECG reading segments may vary. For example, access may be limited to a shorter than desired segment of the ECG. In such cases, certain beat classes may not appear in the local training set. In such a scenario, the local training set may not be useful and can be ignored.

Parameters can be estimated using the global data set. For example, parameter $K_k$ can be used to weigh the local and global training sets, which can also be referred to as classifiers. Parameter $K_k$ can be determined in relation to the number of samples in a give class. For example, $$K_k = \min\left\{\frac{N_k^g}{10}, W\right\},$$

where $N_k^g$ is the number of samples in class k, and the parameter (W) can be set to a particular value (e.g., 0.7).

In some embodiments, to classify the ECG signal, a feature space can be used to describe the signal, and this classification can include binning pulses and data. A feature space can include features extracted from binned data, for example, and binning can include dividing a time domain into equal size bins and counting a number of cardiac events (e.g., heart attack, arrhythmia) that fall within each interval. For example, a time domain of one second can be divided into 10 bins, each having a duration of 1/10 seconds. The bins may or may not include events. For example, one bin may include one cardiac event, and the other bins may include zero cardiac events.

Figure 2:
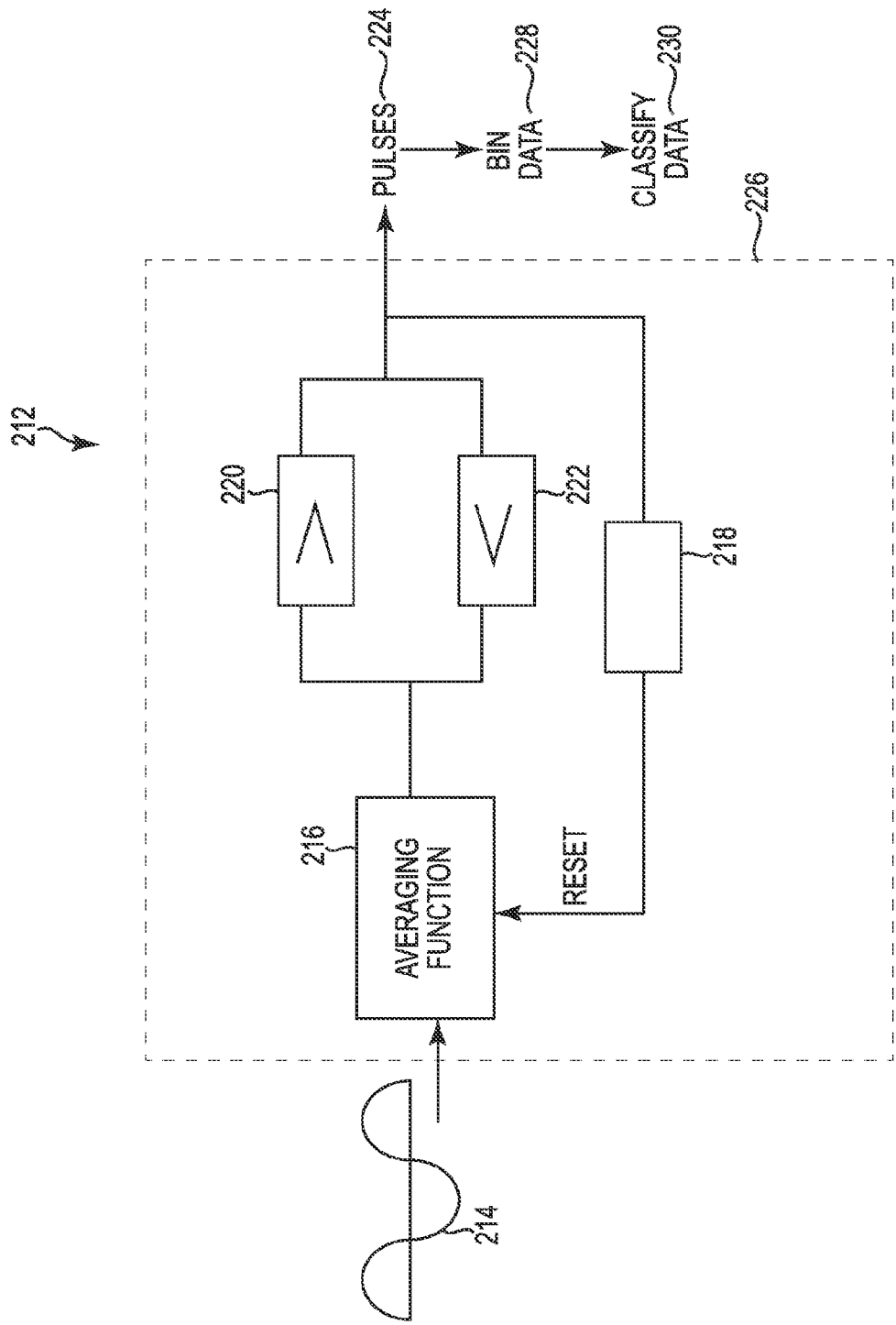
FIG. 2 is a block diagram illustrating an example of a method for classifying an ECG signal according to the present disclosure.

FIG. 2 is a block diagram illustrating an example of a method 212 for classifying an ECG signal according to the present disclosure. At 214, accumulated data and/or an input signal, x, 214 (e.g., an ECG signal) is received by a sampler 226 (e.g., an IF sampler), and the input signal is convolved with an averaging function, u, at 216. Output of the averaging function can be compared against positive and negative thresholds $\theta_p$, and $\theta_n$ at 220 and 222, respectively. If the signal equals or exceeds threshold $\theta_p$ at 220, a pulse can be generated at that time instant at 224. If the signal equals or is less than threshold $\theta_n$ at 222, a pulse can be generated at that time instant at 224. The pulse generated can include a polarity (e.g., a positive or negative polarity) corresponding to the threshold it crossed. For example, crossing threshold $\theta_p$ can result in a pulse with a positive polarity, and crossing threshold $\theta_n$ can result in a pulse with a negative polarity.

Accumulation of data can be reset and held for a particular duration at 218, known as the refractory period, $\tau$. In some embodiments, the refractory period can be adjusted to limit pulse rates independently from an input signal. The accumulated data can then again be convolved with the averaging function. In a number of embodiments, data accumulation can be reset when a particular pulse is generated, for example.

The averaging function with which the accumulated data can be convolved can include:

$$\int x(\alpha)u(\alpha)d\alpha.$$

where, in some examples, $\alpha$ can represent time.

In some embodiments, it can be assumed that support of signal x is compact, and starting at time $t_0$, pulse timings can be defined recursively. For example:

$$\theta_k \int_{t_{k+\tau}}^{t_{k+1}} x(t)e^{\alpha(t-t_{k+1})}dt, \quad \theta \in \{\theta_p, \theta_n\},$$

where u(t) represents a leaky factor in the integration, and $\alpha$, $\tau > 0$. In some examples, k can represent an indexing of the times. For example, k can include a number 1, 2, 3, 4, etc. until the last sample. Since signals and their location are input dependent, a compressed representation for signals can be provided in which information can be localized in increased amplitude transients overlaid on lower amplitude background noise.

The pulses and their data output at 224 can be binned at 228. Binning, as previously discussed herein can include dividing a time domain into a set of non-overlapping intervals and counting a number of events in each interval. An event can include, for example, cardiac events such as heart attacks and arrhythmias, among others. These counts can represent a binned vector, and the representation can maintain a temporal structure of the pulse while providing a vector space representation.

In an example of the present disclosure, a bin size of 35 ms can be used. Different bin sizes can produce different results. For example, a smaller bin size may reduce time jitter, but can result in a higher dimensional space, requiring more samples in a classification task, as compared to a larger bin.

Heartbeats are limited in duration and can be represented as an N dimensional vector, where N is the number of bins. Heartbeat signals can include variability in shape for the same patient and across patients, so information regarding pre- and post-RR intervals can also be included in preprocessing. In order to use this information across patients, normalization can be used and can include the pre- and post-RR intervals, as well as pre- and post-RR intervals normalized by a mean RR interval for a specific patient. A feature vector for any given beat can consist of N counts followed by pre- and post-RR intervals with and without normalization. This can produce an N+4 dimensional feature vector which can be fed into a classifier at 230, such as the LDA classifier discussed previously with respect to FIG. 1 in order to complete classification of an ECG signal and/or signal data.

Figure 3:
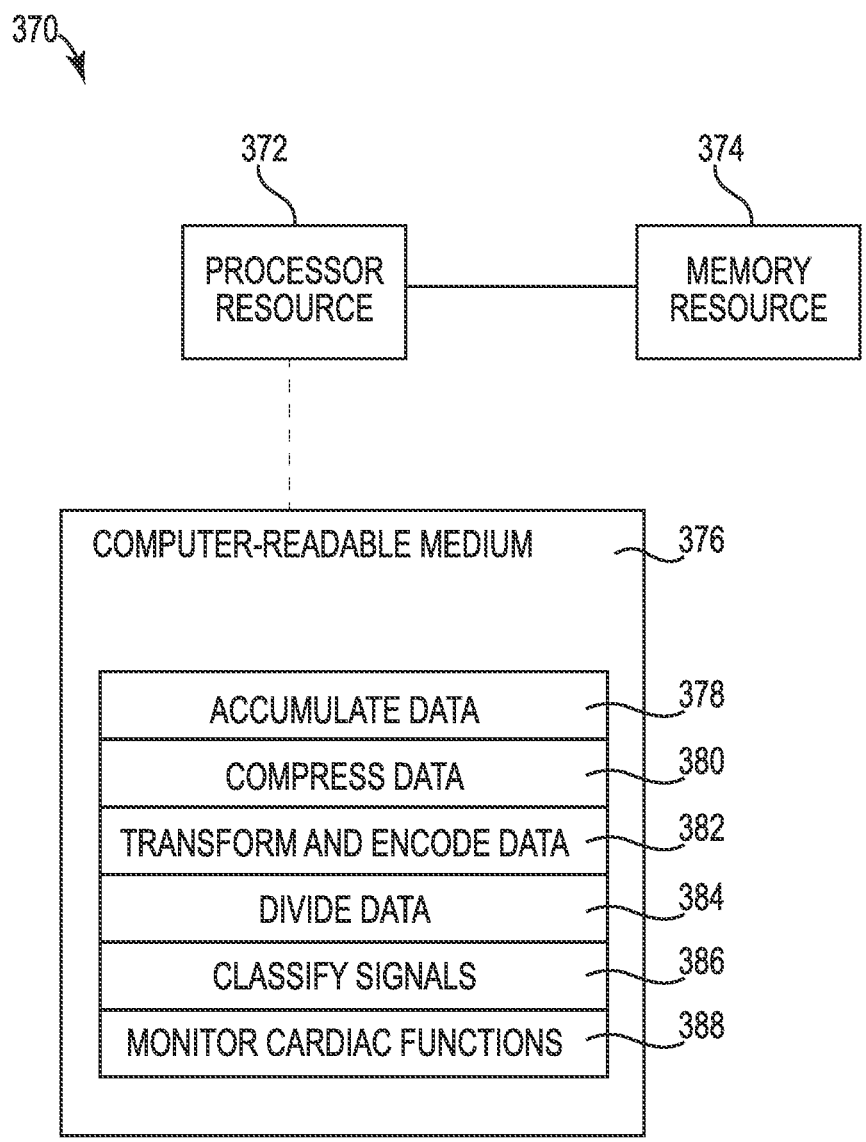
FIG. 3 is a block diagram illustrating a processor resource, a memory resource, and a computer-readable medium according to the present disclosure.

FIG. 3 is a block diagram 370 illustrating a processor resource 372, a memory resource 374, and a computer-readable medium 376 according to the present disclosure. The computer-readable medium (CRM) 376 (e.g., a tangible, non-transitory medium) and/or the memory resource 374 can store a set of instructions executable by the processor resource to accumulate data regarding a number of ECG signals at 378. In some embodiments, the accumulated data can include a pulse generated each time a cardiac event occurs, and the instructions can be executed to reset data accumulation when a particular pulse is generated, for example. The instructions can be executed at 380 to compress the accumulated data.

At 382, the instructions can be executed to transform the compressed accumulated data into a time-based data representation and encode the data representation using an IF sampler. In a number of embodiments, the time-based data representation can include a pulse generated each time a heartbeat is encoded. The instructions can be executed at 384 to divide the data representation into time-based bins, and at 386, the instructions can be executed to classify each of the number of ECG signals based on the separation and the bins. The instructions can be executed at 388 to continuously monitor cardiac functions based on the classifications. Continuously monitoring a patient, for example, can include monitoring and/or sampling a patient for an unbroken time period, (e.g., an hour, a day, a week, etc.) without interruption.

In some embodiments, the instructions can be executed to divide the data representation into a set of non-overlapping time intervals, and the instructions can be executed to calculate a number of cardiac events and/or in each time interval, for example.

In some examples of the present disclosure, the instructions can be executable to pre-process and ECG recording and transform each heartbeat cycle within the ECG recording using an IF sampler. The instructions can further be executable to separate pulse data within each transformed heartbeat cycle into a time-based bin and concatenate the binned pulse data with a particular time interval. In some embodiments, the instructions can be executable to concatenate the binned pulse data with an RR interval. The instructions can be executable to classify an ECG signal of the ECG recording based on the concatenation, for example.

The methods, techniques, systems, and apparatuses described herein may be implemented in digital electronic circuitry or computer hardware, for example, by executing instructions stored in computer-readable storage media. Apparatuses implementing these techniques may include appropriate input and output devices, a computer processor, and/or a tangible computer-readable storage medium storing instructions for execution by a processor.

A process implementing techniques disclosed herein may be performed by a processor executing instructions stored on a tangible computer-readable storage medium for performing desired functions by operating on input data and generating appropriate output. Suitable processors include, by way of example, both general and special purpose microprocessors. Suitable computer-readable storage devices for storing executable instructions include all forms of non-volatile memory, including, by way of example, semiconductor memory devices, such as Erasable Programmable Read-Only Memory (EPROM), Electrically Erasable Programmable Read-Only Memory (EEPROM), and flash memory devices; magnetic disks such as fixed, floppy, and removable disks; other magnetic media including tape; and optical media such as Compact Discs (CDs) or Digital Versatile Disks (DVDs). Any of the foregoing may be supplemented by, or incorporated in, specially designed application-specific integrated circuits (ASICs).

The above specification, examples and data provide a description of the method and applications, and use of the system and method of the present disclosure. Since many examples can be made without departing from the spirit and scope of the system and method of the present disclosure, this specification merely sets forth some of the many possible example configurations and implementations.

Although specific examples have been illustrated and described herein, those of ordinary skill in the art will appreciate that an arrangement calculated to achieve the same results can be substituted for the specific examples shown. This disclosure is intended to cover adaptations or variations of one or more examples of the present disclosure. It is to be understood that the above description has been made in an illustrative fashion, and not a restrictive one. Combination of the above examples, and other examples not specifically described herein will be apparent to those of skill in the art upon reviewing the above description. The scope of the one or more examples of the present disclosure includes other applications in which the above structures and methods are used. Therefore, the scope of one or more examples of the present disclosure should be determined with reference to the appended claims, along with the full range of equivalents to which such claims are entitled.

What is claimed:

1. A non-transitory computer-readable medium comprising instructions for causing a programmable processor to:
   pre-process an electrocardiogram (ECG) recording;
   transform each heartbeat cycle within the ECG recording into pulse data using an Integrate and Fire (IF) sampler;
   separate the pulse data within each transformed heartbeat cycle into a time-based bin;
   concatenate the binned pulse data with a particular time interval; and
   classify an ECG signal of the ECG recording based on the concatenation.

2. The non-transitory computer readable medium of claim 1, wherein the instructions are further cause the programmable processor to concatenate the binned pulse data with an RR interval from the ECG recording.

3. The non-transitory computer readable medium of claim 1, wherein the instructions further cause the programmable processor to:
   create a feature vector which serves as an input to a linear discriminant function; and
   monitor cardiac functions utilizing the linear discriminant function as a linear discriminant classifier.

4. The non-transitory computer readable medium of claim 1, wherein the instructions that cause the programmable processor to preprocess the ECG recording further cause the programmable processor to remove a baseline wander and noise from the ECG recording.

5. A computer-implemented method for classifying an electrocardiogram (ECG) signal, comprising:
   pre-processing an electrocardiogram (ECG) recording;
   transforming each heartbeat cycle within the ECG recording into pulse data using an Integrate and Fire (IF) sampler;
   separating the pulse data within each transformed heartbeat cycle into a time-based bin;
   concatenating the binned pulse data with a pan icular time interval; and
   classifying, via the computer, an ECG signal of the ECG recording based on the concatenation.

6. The method of claim 5, further comprising concatenating the binned pulse data with an RR interval from the ECG recording.

7. The method of claim 5, further comprising:
   creating a feature vector which serves as an input to a linear discriminant function; and
   monitoring cardiac functions utilizing the linear discriminant function as a linear discriminant classifier.

8. The method of claim 5, wherein preprocessing the ECG recording further comprises removing a baseline wander and noise from the ECG recording.

9. A system for classifying an electrocardiogram (ECG) signal, comprising:
   a memory resource; and
   a processing resource coupled to the memory resource, the processing resource configured to:
      pre-process an electrocardiogram (ECG) recording;
      transform each heartbeat cycle within the ECG recording into pulse data using an Integrate and Fire (IF) sampler;
      separate the pulse data within each transformed heartbeat cycle into a time-based bin;
      concatenate the binned pulse data with a particular time interval; and
      classify an ECG signal of the ECG recording based on the concatenation.

10. The system of claim 9, wherein the processing resource is further coupled to the memory resource to concatenate the binned pulse data with an RR interval from the ECG recording.

11. The system of claim 9, wherein the processing resource is further coupled to the memory resource to:
   create a feature vector which serves as an input to a linear discriminant function; and
   monitor cardiac functions utilizing the linear discriminant function as a linear discriminant classifier.

12. The non-transitory computer readable medium of claim 9, wherein the processing resource coupled to the memory resource to preprocess the ECG recording is further coupled to the memory resource to remove a baseline wander and noise from the ECG recording.

* * * * *

UNITED STATES PATENT AND TRADEMARK OFFICE
CERTIFICATE OF CORRECTION

PATENT NO. : 8,706,203 B2  
APPLICATION NO. : 13/459952  
DATED : April 22, 2014  
INVENTOR(S) : Choudur Lakshminarayan et al.

Page 1 of 1

It is certified that error appears in the above-identified patent and that said Letters Patent is hereby corrected as shown below:

In the Claims

In column 8, line 21, in Claim 5, delete "pan icular" and insert -- particular --, therefor.

Signed and Sealed this  
Fifth Day of August, 2014

Michelle K. Lee  
*Deputy Director of the United States Patent and Trademark Office*